United States Patent [19]
Flick et al.

[11] Patent Number: 6,110,856
[45] Date of Patent: *Aug. 29, 2000

[54] CATALYSTS SUITABLE FOR PREPARING ALIPHATIC ALPHA-, OMEGA-AMINONITRILES BY PARTIAL HYDROGENATION OF ALIPHATIC DINITRILES

[75] Inventors: Klemens Flick, Herxheim; Rolf Fischer, Heidelberg; Klaus Ebel, Lampertheim; Werner Schnurr, Herxheim; Guido Voit, Schriesheim, all of Germany

[73] Assignee: BASF Aktiengesellschaft, Ludwigshafen, Germany

[*] Notice: This patent is subject to a terminal disclaimer.

[21] Appl. No.: 09/214,520

[22] PCT Filed: Aug. 21, 1997

[86] PCT No.: PCT/EP97/04547

§ 371 Date: Jan. 7, 1999

§ 102(e) Date: Jan. 7, 1999

[87] PCT Pub. No.: WO98/11058

PCT Pub. Date: Mar. 19, 1998

[30] Foreign Application Priority Data

Sep. 10, 1996 [DE] Germany .................. 196 36 768

[51] Int. Cl.[7] .................. B01J 20/34; C07C 255/04
[52] U.S. Cl. .................. 502/31; 502/260; 558/459
[58] Field of Search .................. 558/459, 452; 502/31, 260

[56] References Cited

U.S. PATENT DOCUMENTS 2,208,598   7/1940   Rigby et al. .
2,257,814  10/1941   Rigby et al. .
5,151,543   9/1992   Ziemecki .................. 558/459
5,527,946   6/1996   Flick et al. .
5,557,004   9/1996   Flick et al. .

FOREIGN PATENT DOCUMENTS 848 654     7/1949   Germany .
42 35 466   4/1994   Germany .
161 419    11/1985   WIPO .
92/21650   12/1992   WIPO .
93/12073    6/1993   WIPO .
93/16034    8/1993   WIPO .
96/18603    6/1996   WIPO .

OTHER PUBLICATIONS

Jrl. Of Cat. 112, 145–156 (1988).

Primary Examiner—Joseph McKane
Assistant Examiner—Ebenezer Sackey
Attorney, Agent, or Firm—Keil & Weinkauf

[57] ABSTRACT

A catalyst suitable for preparing aliphatic alpha, omega-aminonitriles by partial hydrogenation of aliphatic dinitriles comprises
(a) metallic cobalt, a cobalt compound or a mixture thereof, the proportion of metallic cobalt based on (a) being from 20 to 100% by weight,
(b) from 10 to 70% by weight, based on (a), of metallic iron, iron oxide, a further iron compound or a mixture thereof, the proportion of iron oxide based on (b) being from 20 to 100% by weight,
(c) from 0 to 1% by weight, based on (a), of a compound based on an alkali metal, an alkaline earth metal or zinc.

8 Claims, No Drawings

CATALYSTS SUITABLE FOR PREPARING ALIPHATIC ALPHA-, OMEGA- AMINONITRILES BY PARTIAL HYDROGENATION OF ALIPHATIC DINITRILES

This application is a 371 of PCT/EP97/04547 filed Aug. 21, 1997.

The present invention relates to catalysts suitable for the preparation of aliphatic alpha, omega-aminonitriles by partial hydrogenation of aliphatic dinitriles.

It further relates to processes for preparing aliphatic alpha, omega-aminonitriles by partial hydrogenation of aliphatic dinitriles in the presence of such catalysts and to the use of the catalysts for preparing aliphatic alpha, omega-aminonitriles by partial hydrogenation of aliphatic dinitriles.

WO 92/21650 describes the partial hydrogenation of adiponitrile to 6-aminocapronitrile in the presence of a Raney nickel catalyst and ammonia as solvent with a yield of 60% at a conversion of 70%. Hexamethylendiamine is formed as a by-product in a 9% yield. The disadvantage of this process is the short on-stream time of the catalyst.

U.S. Pat. No. 2,257,814 and U.S. Pat. No. 2,208,598 likewise describe processes for preparing 6-aminocapronitrile starting from adiponitrile using Raney cobalt and iron, nickel and cobalt catalysts on various supports. The disadvantages of these processes are the selectivities of 50–60%, which are too low for industrial utilization.

According to the process of WO 93/16034, the yield of aminocapronitrile can be increased by hydrogenating adiponitrile in the presence of Raney nickel, a base such as sodium hydroxide, potassium hydroxide, lithium hydroxide or ammonium hydroxide and a transition metal complex including for example iron, cobalt, chromium or tungsten as transition metal, and a solvent. Reacting within the range from 45 to 60% is said to afford quantitative yields of aminocapronitrile. The disadvantage of this process is the need to recover the usually toxic transition metal complex from the resulting reaction mixture.

EP-A 161,419 describes the partial hydrogenation of adiponitrile using a rhodium catalyst on a magnesium oxide support. A selectivity of 94% is achieved at a conversion of 70%. The disadvantage is the complicated preparation of the Rh/MgO catalysts (see J. Cat. 112 (1988), 145–156).

DE-A 4,235,466 describes the fixed bed hydrogenation of adiponitrile to 6-aminocapronitrile over unsupported iron sponge catalysts prepared from iron ore by a special method and subsequently doped with cobalt, titanium, manganese, chromium, molybdenum, ruthenium or iridium. Owing to their small surface area (0.8 $m^2$/g), these catalysts generally exhibit useful activity only at high pressures and high temperatures. A further disadvantage of this process is the rapid loss of activity: the conversion decreased by 5% over 24 h in Example 7 despite reducing the adiponitrile and hydrogen flow rates, which usually leads to an increase in the conversion.

DE-A 848,654 describes the continuous fixed bed hydrogenation of adiponitrile over palladium on silica gel and over metals of the eighth group of the Periodic Table, these metals preferably being used in the form of spinelums. The essential disadvantage of these catalysts is their satisfactory on-stream time.

It is an object of the present invention to provide suitable catalysts for preparing aliphatic alpha, omega-aminonitriles by partial hydrogenation of aliphatic dinitriles with a high selectivity in respect of the alpha, omega-aminonitriles and in respect of the sum total of alpha, omega-aminonitriles and alpha, omega-diamines.

We have found that this object is achieved by catalysts suitable for preparing aliphatic alpha, omega-aminonitriles by partial hydrogenation of aliphatic dinitriles, comprising
(a) metallic cobalt, a cobalt compound or a mixture thereof, the proportion of metallic cobalt based on (a) being from 20 to 100% by weight,
(b) from 10 to 70% by weight, based on (a), of metallic iron, iron oxide, a further iron compound or a mixture thereof, the proportion of iron oxide based on (b) being from 20 to 100% by weight, The invention further provides processes for preparing aliphatic alpha, omega-aminonitriles by partial hydrogenation of aliphatic dinitriles in the presence of such catalysts and for the use of the catalysts for preparing aliphatic alpha, omega-aminonitriles by partial hydrogenation of aliphatic dinitriles.

Preference is given to those catalysts whose precursor, prior to activation with hydrogen or a gas mixture comprising hydrogen and an inert gas such as nitrogen, comprises one or more cobalt compounds, calculated as cobalt(II) oxide, within the range from 10 to 80% by weight, preferably from 20 to 70% by weight, in particular from 30 to 60% by weight.

Preference is given to those catalysts whose precursor, prior to activation with hydrogen or a gas mixture comprising hydrogen and an inert gas such as nitrogen, comprises one or more iron compounds, calculated as iron(III) oxide, within the range from 20 to 90% by weight, preferably from 30 to 80% by weight, in particular from 40 to 70% by weight.

The catalysts which can be used according to the invention can be supported or unsupported catalysts. Examples of suitable supported materials include porous oxides such as aluminum oxide, silicon dioxide, alumosilicate, lanthanum oxide, titanium dioxide, zirconium dioxide, magnesium oxide, zinc oxide and zeolites and also activated carbon or mixtures thereof.

They are generally prepared by precipitating one or more precursors of component (a) together with precursor of component (b) and, if desired, with one or more precursors of the trace component (c) in the presence or absence of support materials (depending on which catalyst type is desired), if desired processing the resulting catalyst precursor into extrudates or tablets, drying and subsequently calcining. Supported catalysts are generally also obtainable by saturating the support with a solution of components (a), (b) and optionally (c), in which case the individual components can be added simultaneously or in succession, or by spraying components (a), (b) and optionally (c) onto the support in a conventional manner.

Suitable precursors for components (a) and (b) generally include readily water-soluble salts of the aforementioned metals such as nitrates, chlorides, acetates, formates and sulfates, preferably nitrates.

Suitable precursors for component (c) generally include readily water-soluble salts of the alkali metals or alkaline earth metals, such as lithium, sodium, potassium, rubidium, cesium, magnesium or calcium, or zinc and also mixtures thereof, such as hydroxides, carbonates, nitrates, chlorides, acetates, formates and sulfates, preferably carbonates and hydroxides.

The precipitation is generally effected from aqueous solutions, selectively by addition of precipitants, by changing the pH or by changing the temperature.

Suitable precipitants include for example ammonium carbonate or hydroxides or carbonates of the alkali metals. If alkali metal compounds are used as precipitants, it is advisable to free the precipitates from adherent alkali metal compounds by washing with water, for example. This can be carried out directly after the removal of the precipitate from the mother liquor or after a drying and calcining step. Drying can be carried out in a conventional manner, preferably in spray towers, in which case the precipitate is generally suspended in a liquid, advantageously water. The resulting catalyst material is customarily predried, generally at 80–150° C., preferably at 80 –120° C.

The calcining is customarily carried out at 150–500° C., although in individual cases temperatures up to 1000° C. can be suitable, preferably 200–450° C., in a gas stream of air or nitrogen in suitable apparatus such as tray or rotary tube ovens.

The powder can be processed into shaped articles such as extrudates or tablets in a conventional manner, especially if the catalyst material is to be used in a fixed bed.

Extrudates can be produced in the presence of added auxiliaries such as inorganic acids, organic acids or bases such as ammonia, in which case the auxiliaries can comprise cobalt or iron compounds. After extrusion, the extrudates can be dried at below 200° C. and calcined at 150–500° C., although in individual cases temperatures up to 1000° C. can also be suitable, preferably 200–450° C., in a gas stream of air or nitrogen in suitable apparatus such as tray or rotary tube ovens.

Tablets can be produced in the presence of added organic or inorganic auxiliaries such as stearates, graphite or talc.

The catalysts can be used as fixed bed catalysts in the upflow or downflow mode or as suspension catalysts.

Suitable starting materials for the process of the invention are aliphatic alpha, omega-dinitriles of the general formula I

$$NC-(CH_2)_n-CN \quad\quad\quad I$$

where n is an integer from 1 to 10, in particular 2, 3, 4, 5 or 6. Particularly preferred compounds I are succinonitrile, glutaronitrile, adiponitrile, pimelonitrile and suberonitrile, very particular preference being given to adiponitrile.

The process of the invention partially hydrogenates the above-described dinitriles I in the presence of a solvent over a catalyst to obtain alpha, omega-aminonitriles of the general formula II

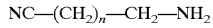

$$NC-(CH_2)_n-CH_2-NH_2 \quad\quad\quad II$$

where n is as defined above. Particularly preferred aminonitriles II are those in which n is 2, 3, 4, 5 or 6, especially 4, ie. 4-aminobutanenitrile, 5-aminopentanenitrile, 6-aminohexanenitrile ("6-aminocapronitrile"), 7-aminoheptanenitrile and 8-aminooctanenitrile, very particular preference being given to 6-aminocapronitrile.

A suspension process is customarily carried out at a temperature within the range from 20 to 150° C., preferably within the range from 30 to 120° C.; the pressure is generally chosen within the range from 2 to 30, advantageously from 2 to 10, preferably from 3 to 10, particularly preferably from 4 to 9, MPa. The residence times are essentially dependent on the desired yield, selectivity and the desired conversion; the residence time is customarily chosen so as to maximize the yield, for example within the range from 50 to 275, preferably from 70 to 200, min. in the case of an adiponitrile feed.

A suspension process is preferably carried out with a solvent selected from ammonia, amines, diamines and triamines having from 1 to 6 carbon atoms such as trimethylamine, triethylamine, tripropylamine and tributylamine or alcohols, especially methanol and ethanol, particularly preferably ammonia. It is advantageous to use a dinitrile concentration within the range from 10 to 90, preferably from 30 to 80, The suspension hydrogenation can be carried out batchwise or, preferably, continuously, generally in the liquid phase.

The partial hydrogenation is preferably carried out batchwise or continuously in a fixed bed reactor in the downflow or upflow mode, for which it is customary to employ a temperature within the range from 20 to 150° C., preferably within the range from 30 to 120° C., and a pressure generally within the range from 2 to 30, preferably within the range from 3 to 20, MPa. The partial hydrogenation is preferably carried out in the presence of a solvent, preferably ammonia, amines, diamines and triamines having 1 to 6 carbon atoms such as trimethylamine, triethylamine, tripropylamine and tributylamine or alcohol, preferably methanol or ethanol, particularly preferably ammonia. In a preferred embodiment, ammonia is used within the range from 0.5 to 10, preferably from 0.5 to 6, g per g of adiponitrile. Here it is preferable to employ a catalyst space velocity within the range from 0.1 to 2.0, preferably from 0.3 to 1.0, kg of adiponitrile/l*h. In this case too the conversion and hence the selectivity can be adjusted in a specific manner through a variation of the residence time.

The process of the invention affords alpha, omega-aminonitriles in good selectivities and with only minimal amounts of hexamethylenediamine. Furthermore, the catalysts used according to the invention have a distinctly longer on-stream time than comparable catalysts from the prior art. alpha, omega-Aminonitriles are important starting compounds for preparing cyclic lactams, especially 6-aminocapronitrile for caprolactam.

EXAMPLES

The phase compositions of the catalysts were determined by XRD.

The key to the abbreviations used is:
ADN=adipolinitrile [sic], HMD=hexamethylenediamine, ACN=6-aminocapronitrile

Inventive Example 1

A tubular reactor 1800 mm in length and 30 mm in internal diameter was charged with 740 ml (720 g) of a catalyst consisting of 48% of CoO, 0.6% of $Na_2O$, the balance being $Fe_2O_3$. The catalyst was activated in a hydrogen/nitrogen stream at 230° C. under atmospheric pressure. Initially the $N_2$ rate was 450 1/h and the $H_2$ rate 50 l/h. Over the next 8 h the $H_2$ content of the reducing gas was progressively raised to 100%. After 8 h, the reducing stream was pure hydrogen. This was followed by a further 12 h of activation with 500 l/h of $H_2$ at 250° C. under atmospheric pressure.

After the temperature had been reduced to 65° C. (inlet) or 80° C. (outlet), the reactor was fed at 200 bar with a mixture of 400 ml/h of adiponitrile, 640 ml/h of ammonia and 500 l/h of hydrogen by the upflow procedure. To remove the heat of reaction, 4 of 5 l of the reactor effluent were cooled and recycled into the reactor. Under these conditions, the conversion of the adiponitrile is 75%. The reaction mixture consisted essentially of 25% of ADN, 37% of ACN and 37% of HMD. After 2600 h the catalyst still performed to the same selectivity as the fresh catalyst and with unchanged activity.

The metallic cobalt content of component (a) was 50% by weight, and the iron oxide content of component (b) 30% by weight.

Comparative Example 1

Three serially connected tubular reactors (total length 4.5 m, d=6 mm) were charged with 90 ml (107 g) of the catalyst of Example 1 and then reduced in a 200 l/h hydrogen stream under atmospheric pressure. For this, the temperature was raised from 50° C. to 340° C. over 24 h and then held at 340° C. for 72 h. After the temperature had been lowered to 110° C., the reactor was fed at 200 bar with a mixture of 50 ml/h of ADN, 280 ml of $NH_3$ and 200 standard l/h of $H_2$. No conversion was achieved.

The metallic cobalt content of component (a) was 90% by weight, and the iron oxide content of component (b) 16% by weight.

Comparative Example 2

Three serially connected tubular reactors (total length 4.5 m, d=6 mm) were charged with 90 ml (107 g) of the catalyst of Example 1 and then reduced in a 200 l/h hydrogen stream under atmospheric pressure. For this, the temperature was raised from 50° C. to 200° C. over 3 h and then held at 200° C. for 12 h. After the temperature had been lowered to 75° C., the reactor was fed at 200 bar with a mixture of 50 ml/h of ADN, 280 ml of $NH_3$/h and 200 standard l/h of $H_2$. An ADN conversion of 50% was achieved under these conditions. The reaction mixture consisted essentially of 50% of ADN, 40% of ACN and 10% of HMD. Such a reactor effluent was obtained over a period of 300 h. After 300 h, the feeds were stopped except for $NH_3$ and $H_2$. After a rinsing period of 12 h, the $NH_3$ feed was stopped as well, and the catalyst was reactivated with 200 l/h of $H_2$ at 340° C. under atmospheric pressure over 72 h. For this, the temperature was raised from 50° C. to 340° C. over 24 h and then held at 340° C. for 72 h. After the temperature had been lowered to 80° C., the reactor was fed at 250 bar with a mixture of 50 ml/h of ADN, 230 ml/h of $NH_3$ and 200 ml/h of $H_2$. No conversion was achieved under these conditions and after raising the temperature to 120° C.

We claim:

1. A catalyst suitable for preparing aliphatic alpha, omega-aminonitriles by partial hydrogenation of aliphatic dinitriles, comprising
    (a) metallic cobalt, or a mixture of metallic cobalt and a cobalt compound, the proportion of metallic cobalt based on (a) being from 20 to 100% by weight,
    (b) from 10 to 70% by weight, based on (a), of metallic iron, iron oxide, a further iron compound or a mixture thereof, the proportion of iron oxide based on (b) being from 20 to 100% by weight,
    (c) from 0 to 1% by weight, based on the sum of (a) and (b), of a compound based on an alkali metal, an alkaline earth metal or zinc.

2. A catalyst as claimed in claim 1 in the form of an unsupported catalyst.

3. A catalyst as claimed in claim 1 in the form of a supported catalyst.

4. A process for preparing aliphatic alpha, omega-aminonitriles by partial hydrogenation of aliphatic dinitriles at elevated temperature and elevated pressure in the presence of a catalyst as claimed in claim 1.

5. A process as claimed in claim 4, wherein the hydrogenation is effected in a fixed bed reactor.

6. A process as claimed in claim 4, wherein adiponitrile is used as the alpha, omega-dinitrile to obtain 6-aminocapronitrile.

7. A process as claimed in claim 1, wherein the hydrogenation is carried out at a pressure within the range from 2 to 30 MPa.

8. A process as claimed in claim 1, wherein the hydrogenation is carried out at a temperature within the range from 20 to 150° C.

* * * * *